United States Patent [19]

Le Van Mao et al.

[11] 4,366,135

[45] Dec. 28, 1982

[54] METHOD FOR PREPARING ZEOLITES

[75] Inventors: Raymond Le Van Mao; Orlando Pilati, both of Milan; Enrico Moretti, Bollate; Romano Covini, Milan; Fausto Genoni, Samarate, all of Italy

[73] Assignee: Montedison S.p.A., Milan, Italy

[21] Appl. No.: 214,763

[22] Filed: Dec. 9, 1980

Related U.S. Application Data

[63] Continuation-in-part of Ser. No. 163,103, Jun. 26, 1980, abandoned.

[30] Foreign Application Priority Data

Jun. 29, 1979 [IT] Italy .............................. 23978 A/79

[51] Int. Cl.$^3$ .............................................. C01B 33/28
[52] U.S. Cl. ............................. 423/329; 252/431 N; 252/455 Z; 423/328; 546/11
[58] Field of Search ................................ 423/328–330; 252/431 N, 455 Z; 546/11

[56] References Cited

U.S. PATENT DOCUMENTS 3,702,886 11/1972 Argauer et al. ..................... 423/328
4,000,248 12/1976 Martin ................................. 423/329
4,205,053 5/1980 Rollmann et al. .................. 423/329
4,251,499 2/1981 Nanne et al. ....................... 423/329

*Primary Examiner*—Edward J. Meros

[57] ABSTRACT

Preparation of zeolites having the formula:

$$(1.5 \pm 0.6)\ M_{2/n}O \cdot Al_2O_3 \cdot y SiO_2 \cdot z H_2O$$

[wherein y ranges from 20 to 90, z ranges from 2 to 12, M is at least one cation and n is the valence of M], comprising the admixing of diethyl-piperidinium hydroxide, or a salt thereof, with $H_2O$ and with at least one Na compound, one Al compound and one Si compound, the molar ratios (ratios of oxides) being:
$SiO_2:Al_2O_3$ = from 20 to 120;
$H_2O:Na_2O$ = from 50 to 600;
$Na_2O:SiO_2$ = from 0.07 to 0.50;
$(DEPP)_2O:SiO_2$ = from 0.05 to 0.50.

The invention concerns also the thus obtained zeolites and their use for acid-catalyzed conversions of hydrocarbons.

10 Claims, No Drawings

METHOD FOR PREPARING ZEOLITES

This application is a continuation-in-part of application Ser. No. 163,103 filed on June 26, 1980, now abandoned.

BACKGROUND OF THE INVENTION

The prior art described synthetic zeolites, different methods of preparing same and the use of synthetic or natural zeolites in the catalytic conversion of hydrocarbons. The zeolites according to the invention are very stable to heat and acids, what makes them particularly suited for processes involving high temperatures, such as isomerization of xylenes; other advantages will appear from the description.

DESCRIPTION OF THE INVENTION

The invention relates to a method for preparing zeolites having the formula: $(1.5\pm0.6)$ $M_{2/n}$ $O.Al_2O_3.ySiO_2.zH_2O$, where y ranges from 20 to 90, preferably from 40 to 80 and z from 2 to 12, preferably from 3 to 8, M is at least one cation and n is the valence of M, and where Al and Si may be optionally replaced, at least partially, by Ga and Ge respectively. M is preferably selected from the monovalent cations, the cations of the rare earths, the cations of the 2nd and 8th Groups of the Periodic System, and mixtures thereof; in particular the cations can be selected from alkaline ions, hydrogen ion, ammonium ion, diethyl-piperidinium ion and mixtures thereof. The formula of diethyl-piperidinium ion (DEPP)+ is:

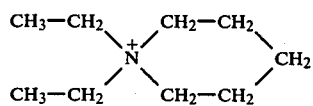

The method according to the invention comprises the admixture of (DEPP)OH or of a salt thereof with $H_2O$ and with at least one compound containing Na, one compound containing a metal selected from amongst Al, Ga and mixtures thereof and one compound containing an element selected from amongst Si, Ge and mixtures thereof, the molar ratios, expressed as oxides ratios, being comprised in the following ranges;

$SiO_2:Al_2O_3$ = from 20 to 120 (preferably from 40 to 85)
$Na_2O:SiO_2$ = from 0.07 to 0.50 (preferably from 0.07 to 0.25)
$(DEPP)_2O:SiO_2$ = from 0.05 to 0.50 (preferably from 0.10 to 0.20)
$H_2O:Na_2O$ = from 50 to 600 (preferably from 150 to 400).

According to a preferred embodiment, the cation dilution ratios, namely the molar ratios:
r1 = $H_2O:(DEPP)_2O$ (organic cation ratio)
r2 = $H_2O:[(DEPP)_2O+Na_2O]$ (global cation ratio) are respectively equal to or higher than 160 (preferably 190) and 80 (preferably 90) and the r2:r1 ratio (namely the sodium factor SF) is equal to or lower than 0.6 (preferably between 0.20 and 0.60). A very important factor, the cation mineralization factor (CMF), defined as:

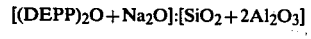

should be higher than 0.20 (preferably from 0.22 to 0.38).

The synthesis can be carried out under autogenous pressure, in an autoclave equipped with stirrer, in one or more steps at, between 130° to 200° C. for one or more days, and preferably between 160° to 200° C.; the solid is then separated from the liquid, for instance by filtration or centrifugation. Sources of Si, Al, Ga, Ge and Na can be compounds providing for the corresponding oxides, such as Al silicates, Na aluminates, Na silicates, silica hydrosol, silica gel, silicic acid and NaOH; (DEPP)++ ion can be provided for by the hydroxide, a halide (in particular bromide or iodide), a sulphate, a phosphate or the nitrate. Zeolites can undergo exchange of the original ion with the proton (from acids) or with the ammonium ion; it is possible to obtain zeolites in the acid form by exchange with ammonium (using for instance $NH_4Cl$, $NH_4NO_3$ or $NH_4OH$) and by successive calcination of the zeolite. The ammonium ion decomposes and a proton is left in the structure; the protons (or the original ions) can be exchanged with all the cations of the Periodic System, in particular with the cations of the 8th group, according to known technologies. The new zeolites can be used in acid form or partially exchanged with different ions; it is possible to add active components by means of known techniques, such as dry or wet impregnation and mechanical mixing.

Zeolites can be prepared in a variety of shapes, for instance in granules or extrudates; in such cases it is advisable to admix the obtained powder with a binding material, such as clays, silica, alumina or other metal oxides. Before being used, zeolites should be at least partially dehydrated, for example by a heat-treatment at high temperatures, under vacuum or not; activation in the air, at temperatures from 450° C. to the temperature at which the structural collapse of the zeolite starts (about 850° C.) is recommendable.

The invention relates also to the use of the new zeolites for the conversion of hydrocarbons by means of acid-catalyzed reactions, such as cracking, hydrocracking, isomerization, aromatization, polymerization, reforming, alkylation, disproportionation and dealkylation, for which reactions a very high activity and selectivity have been determined.

When zeolites are used as catalysts, it is advisable to mix them with a binder such as silica, alumina, clays (in particular bentonite), metal oxides and in general all the binders considered in U.S. Pat. No. 3,702,886.

In such a case moreover, one can add metals having hydrogenating properties, like Ni or other metals of the VIII group, which can be added either by exchange or impregnation or by any other known technology. They lower the fouling of the catalyst and cause its life to be longer.

Best results have been obtained in the isomerization of meta-xylene to ortho and para isomers; isomerization of meta-xylene, optionally in admixture with ethylbenzene and with lower amounts of desired products (ortho- and para-xylene), can be carried out in vapor phase, in the presence of hydrogen (molar ratio $H_2$/hydrocarbon from 3 to 10), at temperatures from 250° to 450° C., preferably from 275° to 420° C., at pressures from 10 to 20 kg/cm² and at space velocities from 1 to 10 volumes of liquid hydrocarbon per apparent volume of catalyst and per hour (LHSV = from 1 to 10, preferably from 2 to 8 h⁻¹).

The following examples illustrate the invention, without being however a limitation thereof.

CONDITIONS COMMON TO ALL THE EXAMPLES

X-rays analysis was carried out by the powder diffraction method, using a wide-angle diffractometer equipped with a proportional counter with a discriminator of the pulse-height, using the $K_\alpha$ radiation of copper ($\lambda = 1.54178$ Å), filtered with a nickel foil, and using the followng conditions:

| | |
|---|---|
| scanning rate: | $1° \text{ min}^{-1}$, $\frac{1}{4}° \text{ min}^{-1}$ |
| divergence slit: | $\gamma = 1°$ |
| receiving slit: | $\nu = 0.1$ mm |
| time constant | 4 seconds. |

Heights I and angular positions of the diffraction peaks were deduced from the diffractograms; relative intensities 100 $I/I_o$ and interplanar distances "d" expressed in Ångstrom were determined on the basis of height $I_o$ of the most intense diffraction peak and of diffraction angle $2\theta$ of the recorded lines. Angle $2\theta$, indicated by the goniometer, was calibrated by means of reflections (111), (311) and (620) of a high purity silicon standard ($a_o = 5.43088$ Å). The exchange of $Na^+$ ion with other cations and the activation treatment at 540° C. provided crystalline products; the X-rays pattern did not show substantial variations, with respect to the $Na^+$ form, but for a few little shifts in interplanar distances and for the relative intensities of the bands. The adsorption properties of zeolites towards vapors help to point out their structures, as suggested by Landolt G. R. [Anal. Chem. 43 (4), 613 (1971)]. As to the adsorption, $H_2O$, n-hexane and cyclohexane contact zeolite samples (degasified at 350° C. under vacuum) at 25° C., under a pressure lower than their vapor pressure at 25° C. (22 torr for $H_2O$, 45 torr for n-hexane and 28 torr for cyclohexane). Difference of weight before and after adsorption indicated the value of the adsorption.*

*R. Le Van.Mao, React. Kinet Catal. Lett., Vol. 12 (1) 69–76 (1979)

EXAMPLE 1

75 g of (DEPP) Br, 3 g of Na aluminate and 7.5 g of NaOH were dissolved in 300 cm³ of $H_2O$. The solution was heated at 60°–70° C., whereupon 225 g of silica sol (Ludox AS) were added, and then again at a temperature from 60° to 70° C. under intense stirring for 10 minutes. Ludox AS is a colloidal aqueous solution containing 30.5% by weight of silica and 0.25% by weight of ammonia. The composition (by mols) was:

| | | |
|---|---|---|
| $SiO_2 = 1.144$ | $Na_2O = 0.113$ | (DEPP)Br = 0.338 |
| $Al_2O_3 = 0.017$ | $H_2O = 25.4$ | |

The gel was transferred into a Hastelloy C autoclave and heated at 150° C. for 8 days and then at 175° C. for 5 days, under stirring (30 rpm). After cooling, the suspension was discharged and filtered; the solid was washed until the washing liquid had a pH value lower than 9 and then dried at 120° C. for 12 hours.

The product was crystalline and exhibited the X-rays pattern of Table 1; its chemical composition was (% by weight):

| | | |
|---|---|---|
| Si = 40.7 | Na = 0.9 | C = 5.7 |
| Al = 1.2 | H = 1.5 | N = 0.7 |

After activation in the air at 540° C. for 10 hours, the solid exhibited the following vapor adsorption at 25° C.:

| | | |
|---|---|---|
| water | = 10.4 b.w. | |
| n-hexane | = 8.7 b.w. | cyclohexane = 5.4 b.w. |

EXAMPLE 2 (acid form)

The compound, washed and dried at 120° C. (but not activated) as in example 1, was poured into a flask equipped with a reflux cooler, in contact with an aqueous solution of $NH_4Cl$ at 5% by weight, using 19 cm³ of solution per gram of zeolite. Under moderate stirring, the flask was heated at from 70° to 80° C. and kept at such temperature for 1 hour; after decantation, the operation was repeated four times using a fresh solution of $NH_4Cl$. At the end the compound was washed with distilled water until disappearance of the $Cl^-$ ions in the washing liquid, and dried at 120° C. for 12 hours. Its composition (% by weight) was:

| | | |
|---|---|---|
| Si = 41.7 | Na = 0.2 | C = 5.2 |
| Al = 1.0 | H = 0.9 | N = 0.8 |

By activation of the compound in the air at 540° C. for 10 hours, the acid form or "H-zeolite" was obtained; the X-rays diffraction pattern is reported on Table 2.

EXAMPLE 3

2.0 g of Na aluminate, 50 g of (DEPP) Br and 5 g of NaOH were dissolved in 200 cm³ of $H_2O$. We heated at 60° C. and 150 g of silica sol (Ludox AS) were added; after intense stirring for 10 minutes, the gel, having the following composition by moles:

| | | |
|---|---|---|
| $SiO_2 = 0.763$ | $Na_2O = 0.075$ | (DEPP) Br = 0.225 |
| $Al_2O_3 = 0.011$ | $H_2O = 16.9$ | | was transferred into the autoclave of example 1, where it was heated at 150° C. for 8 days and then at 190° C. for 6 days.

After discharge, the solid was washed and dried as in example 1. The product exhibited the diffraction pattern recorded in Table 3; its chemical composition (% by weight) was:

| | | |
|---|---|---|
| Si = 41.1 | Na = 0.5 | C = 5.4 |
| Al = 1.15 | H = 0.6 | N = 0.7 |

The solid, activated as in example 1, exhibited the following

| | |
|---|---|
| vapor adsorption at 25° C.: | water = 9.6% b.w. |
| n-hexane = 8.2% b.w. | cyclohexane = 4.5% b.w. |

EXAMPLE 4 (acid form)

The product, washed and dried at 120° C. (but not activated) as in example 3, was exchanged with $NH_4^+$ (see example 2) and dried at 120° C. for 12 hours. Its composition was (% by weight):

| Si = 41.7 | Na = 0.2 | C = 5.0 |
|---|---|---|
| Al = 1.15 | H = 0.8 | N = 0.8 |

By activation of the compound as in example 2, the "H-zeolite" was obtained; the product, in acid form, showed the X-rays diffraction pattern of Table 4.

EXAMPLE 5

50 g of (DEPP) Br, 2 g of Na aluminate and 5 g of NaOH were dissolved in 250 cm$^3$ of H$_2$O; the solution was heated at 60°–70° C., whereupon 150 g of silica sol (Ludox AS) were added. Heating of the mixture at 60°–70° C. was carried on under intense stirring for 10 minutes. The composition (by moles) was:

| SiO$_2$ = 0.763 | Na$_2$O = 0.075 | (DEPP) Br = 0.225 |
|---|---|---|
| Al$_2$O$_3$ = 0.011 | H$_2$O = 19.7 | |

The gel was poured into the autoclave of example 1 and heated at 150° C. for 9 days and then at 180° C. for 5 days under stirring (30 rpm). After cooling, the suspension was discharged and filtered; the solid was washed and dried as in example 1. The product revealed the diffraction pattern shown in Table 5. Its composition was (% by weight):

| Si = 40.1 | Na = 0.9 | C = 4.4 |
|---|---|---|
| Al = 0.9 | H = 0.4 | N = 0.6 |

The solid, activated as in example 1, exhibited the following

| water = 7.8% b.w. | | |
|---|---|---|
| n-hexane = 5.7% b.w. | cyclohexane = 4.3% b.w. | |

EXAMPLE 6 (acid form)

The product, washed and dried at 120° C. (but not activated) as in example 5, was exchanged with NH$_4$+ (see example 2) and dried at 120° C. for 12 hours. Its composition was (% by weight):

| Si = 42.5 | Na = 0.2 | C = 3.9 |
|---|---|---|
| Al = 1.0 | H = 0.5 | N = 0.7 |

By activation of the product as in example 2, the "H-zeolite" was obtained; the product, in acid form, showed the X-rays diffraction pattern of Table 6.

EXAMPLE 7

The zeolites in the acid form obtained in examples 2, 4 and 6 were mixed with 10% by weight of bentonite, homogenously kneaded with a suitable amount of water and extruded in pieces having a diameter of 1 mm; the product was then dried for 12 hours between 100° and 120° C. and for 2 hours at 540° C. The resulting catalyst was used in the isomerization of meta-xylene, either as such or in admixture with about 10% by weight of ethylbenzene (see Table 7). To this purpose, 30 cm$^3$ of catalysts were charged into a steel reactor having an inside diameter of 16 mm, electrically heated; test conditions and results obtained are recorded in Table 7. High approaches to thermodynamic equilibrium are reached, the reaction product consisting essentially of C$_8$ aromatics, benzene, toluene and higher polyalkylaromatics (having more than 8 carbon atoms); non aromatic liquid products, generally derived from the hydrogenation of the aromatic nucleus, were present in negligible amounts, while gaseous products (for instance CH$_4$) were not revealed by the gaschromatographic analysis. Approach to thermodynamic equilibrium means (% by weight):

$$\frac{\% \text{ of p-xylene flowing out} - \% \text{ of p-xylene flowing in}}{\% \text{ of p-xylene at equilibrium} - \% \text{ of p-xylene flowing in}} \times 100$$

The percentage of para-xylene at equilibrium is calculated in the 3-components system; no ethylbenzene was obtained from the xylenes.

EXAMPLE 8

90 g of (DEPP) Br, 4.5 g of Na aluminate and 15.8 g of NaOH were dissolved in 675 cm$^3$ of H$_2$O. The solution was heated at 60°–70° C., whereupon 330 g of silica sol (Ludox HS) were added, and then heated again at from 60° to 70° C. under intense stirring for 10 minutes. Ludox HS is a colloidal aqueous solution containing 30.5% by weight of SiO$_2$ and 0.32% Na$_2$O as stabilizer; the resulting mixture had the following composition by mols:

| SiO$_2$ = 1.678 | Na$_2$O = 0.242 | (DEPP)Br = 0.405 |
|---|---|---|
| Al$_2$O$_3$ = 0.025 | H$_2$O = 50.3 | |

The gel was transferred into the autoclave of example 1 and heated at 190° C. for 4 days in only one step under stirring (30 rpm). After cooling, the suspension was discharged and filtered; the solid was washed and dried as in example 1. The product was crystalline; its composition was (% by weight):

| Si = 42.6 | Na = 0.4 | C = 3.4 |
|---|---|---|
| Al = 0.9 | H = 0.4 | N = 0.4 |

The product revealed the diffraction pattern shown in Table 8. The solid activated as in example 1 exhibited the following vapor adsorption at 25° C.:

| water = 5.8% b.w.; | n-hexane = 4.9% b.w.; | cyclohexane = 2.7% b.w. |
|---|---|---|

The compound, washed and dried at 120° C., was exchanged with NH$_4$+ as in example 2. At the end the compound was washed and dried as in example 2. Its composition (% by weight) was:

| Si = 42.5 | Na = 0.2 | C = 3.3 |
|---|---|---|
| Al = 1.1 | H = 0.4 | N = 0.7 |

By activation as in example 2, the "H-zeolite" was obtained. 35.8 parts by weight of such zeolite in acid form were admixed with 3.6 parts b.w. of bentonite and homogeneously kneaded with a solution obtained by dissolving 2.15 parts b.w. of nickel nitrate (hexahydrate)

in 25 parts b.w. of H₂O; the whole was extruded into granules having a diameter of 1 mm.

The product was dried for 12 hours between 110° and 120° C. and activated for 2 hours at 540° C. 30 cm³ of the thus obtained catalyst were loaded into the reactor of example 7; test conditions and results are recorded in Table 7.

Zeolites, prepared according to this example and to other examples using DEPP++ cation, were indicated by us as "MB-28" zeolites. The characterizing molar ratios of starting solutions compositions of examples 1, 3, 5, 8 and 10 are reported in the following table:

| Ex. | $r_1 = \frac{H_2O}{(DEPP)_2O}$ | $r_2 = \frac{H_2O}{(DEPP)_2O + Na_2O}$ | $SF = r_2/r_1$ | $CMF = \frac{(DEPP)_2O + Na_2O}{SiO_2 + 2Al_2O_3}$ |
|---|---|---|---|---|
| 1 | 150 | 90 | 0.60 | 0.24 |
| 3 | 150 | 90 | 0.60 | 0.24 |
| 5 | 175 | 105 | 0.60 | 0.24 |
| 8 | 248 | 113 | 0.46 | 0.26 |
| 10 | 249 | 150 | 0.60 | 0.22 |

It is worthwhile to note that $r_1$ (organic cation ratio) and $r_2$ (global cation ratio) of examples 8 and 10 are rather high, with respect to the corresponding ratios of examples 1, 3 and 5; in particular, for the present example 8 the $r_2/r_1$ (sodium)factor is lower than for the other examples (<0.5). The CMF (cation mineralization factor) is quite similar for all the examples.

EXAMPLE 9

The "H form" for the zeolite prepared according to example 8 was tested in an apparatus as in example 7 and at the beginning the results were better, but after a few hundreth of hours lower results were obtained, with respect to the nickel impregnated zeolite tested in example 8; it is clear that nickel exerts a beneficial action on the catalyst life.

EXAMPLE 10

50 g of (DEPP)Br and 2 g of Na aluminate were dissolved in 400 cm³ of H₂O. The solution was heated at 60°–70° C., whereupon 15 g of an aqueous solution of sodium silicate and 150 g of silica sol (Ludox HS) were added; the silicate solution contained 20% by weight SiO₂ and 23% by weight Na₂O, which practically corresponds to the formula of metasilicate. We heated again at from 60° to 70° C. under intense stirring for 10 minutes. The solution had the following composition by mols:

| $SiO_2$ = 0.813 | $Na_2O$ = 0.075 | (DEPP) Br = 0.225 |
|---|---|---|
| $Al_2O_3$ = 0.011 | $H_2O$ = 28.1 | |

The gel was transferred into the autoclave of example 1 and heated at 170° C. for 7 days, under stirring (30 rpm). After cooling, the suspension was discharged and filtered; the solid was washed and dried as in example 1; its composition was (% by weight):

| Si = 39.9 | Na = 0.5 | C = 6.9 |
|---|---|---|
| Al = 1.0 | H = 1.1 | N = 0.9 |

The solid, activated as in example 1, exhibited the following vapor adsorption at 25° C.;

water=10.1% b.w.; n-hexane=9.5% b.w.; cyclohexane=5.0% b.w.

The compound, washed and dried at 120° C., was exchanged with NH₄+ as in example 2. At the end the compound was washed and dried as in Example 1. Its composition (% by weight) was:

| Si = 41.2 | Na = 0.2 | C = 6.5 |
|---|---|---|
| Al = 1.0 | H = 0.8 | N = 0.9 |

By activation as in Example 2, the "H-zeolite" was obtained; 30 g of such "H form" of the zeolite were admixed with 3 g of bentonite and homogeneously Kneaded with 25 cm³ of H₂O; the whole was then extruded into granules having a diameter of 1 mm. The granules were dried for 12 hours between 110° and 120° C. and activated again for 2 hours at 540° C. 30 cm³ of catalyst were loaded into the reactor of example 7; test conditions and results are reported on Table 7.

EXAMPLE 11

The catalyst of example 10 was regenerated in air at 540° C. for 16 hours and 15.5 g of the regeneraed granules were impregnated with 18 cm³ of an aqueous solution containing 0.85 g of Ni(NO₃)₂.0.6H₂O. After drying at 120° C. for 12 hours the granules were loaded in the reactor of example 7 and identical conditions were used as in example 10. The results are reported in Table 7. The best performance, when nickel is present, is reached after many hours, which is an index of stability and long life.

EXAMPLE 12

60 g of (DEPP)Br, 3 g of Na aluminate and 10.5 g of NaOH were dissolved in 450 cm³ of H₂O. The solution was heated at 60°–70° C., whereupon 150 g of silica sol (Ludox HS) were added, and then heated again at a temperature from 60° to 70° C. under intense stirring for 10 minutes. The composition by moles was:

| $SiO_2$ = 0.763 | $Na_2O$ = 0.157 | (DEPP)Br = 0.270 |
|---|---|---|
| $Al_2O_3$ = 0.017 | $H_2O$ = 30.8 | |

The following molar ratios and factors were used: $r_1$=228; $r_2$=105; SF=0.46; CMF=0.37

It is worthwhile to note that CMF (cation mineralization factor) of this example is higher than previous examples.

The gel was transferred into the autoclave of example 1 and heated at 190° C. for 4 days under stirring (30 rpm). After discharge, the solid was washed and dried as in example 1. The product was crystalline and exhibited the X-rays pattern of Table 9; its chemical composition was (% by weight):

| Si = 40.4 | Na = 0.7 | C = 4.9 |
|---|---|---|

| Al = 1.3 | H < 0.1 | N = 0.7 |

After activation as in example 1, the solid exhibited the following vapor adsorption at 25° C.:

| water | = 9.4 b.w. | |
| n-hexane | = 6.7 b.w. | cyclohexane = 4.1 b.w. |

The compound, washed and dried at 120° C. (but not activated) was exchanged with $NH_4^+$ (see example 2) and dried at 120° C. for 12 hours. Its composition was:

| Si = 40.7% b.w. | Na = 0.1% b.w. | C = 4.9% b.w. |
| Al = 1.5% b.w. | H < 0.1% b.w. | N = 1.0% b.w. |

By activation of the compound as in example 2, the "H zeolite" was obtained.

EXAMPLE 13

75 g of (DEPP)Br, 3 g of Na aluminate and 12 g of NaOH were dissolved in 450 cm³ of $H_2O$. The solution was heated at 60°–70° C., whereupon 205 g of silica sol (Ludox HS) were added, and then heated again at a temperature from 60° to 70° C. under intense stirring for 10 minutes. The composition (by moles) was:

| $SiO_2$ = 1.042 | $Na_2O$ = 0.179 | (DEPP)Br = 0.338 |
| $Al_2O_3$ = 0.017 | $H_2O$ = 33.0 | | which corresponds to the following ratios and factors:

| r1 = 195 | r2 = 95 | SF = 0.49 | CMF = 0.32 | also in this example, the CMF factor is very high.

The gel was transferred into the autoclave of example 1 and heated at 190° C. for 4 days under stirring (30 rpm). After discharge, the solid was washed and dried as in example 1. The product was crystalline and exhibited the X-rays pattern of Table 10; its chemical composition was (% by weight):

| Si = 42.6 | Na = 0.5 | C = 4.1 |

| Al = 1.0 | H = 0.5 | N = 0.5 |

After activation as in example 1, the solid exhibited the following vapor adsorption at 25° C.;

| water | = 7.3 b.w. | |
| n-hexane | = 5.8 b.w. | cyclohexane 3.9 b.w. |

The compound, washed and dried at 120° C. (but not activated) was exchanged with $NH_4^+$ (see example 2) and dried at 120° C. for 12 hours. Its composition was:

| Si = 42.1% b.w. | Na = 0.2% b.w. | C = 3.9% b.w. |
| Al = 1.0% b.w. | H = 0.9% b.w. | N = 0.7% b.w. |

By activation of the compound as in example 2, the "H zeolite" was obtained.

EXAMPLE 14

The zeolite in the acid form obtained in examples 12 and 13 were mixed with 10% by weight of bentonite, homogenously kneaded with a suitable amount of $H_2O$ and extruded in pieces having a diameter of 1 mm; the product was then dried for 12 hours between 110° and 120° C. and for 2 hours at 540° C. The resulting catalyst was used in the isomerization of meta-xylene. 30 cm³ of catalyst were charged into the reactor of example 7; test conditions and results are recorded in Table 11, where "AEQT para" is the approach to thermodynamic equilibrium, calculated on the basis of the paraxylene amounts and described in example 7. The other two expressions "AEQT meta" and "AEQT ortho" in Table 11 have been obtained by replacing the paraxylene amounts, in the formula of example 7, respectively by the corresponding amounts of metaxylene and orthoxylene.

EXAMPLE 15 (Endurance test)

18.2 parts by weight of the H zeolite of example 12 were mixed with 0.8 parts by b.w. of bentonite and homogeneously kneaded with a solution obtained by dissolving 1.04 parts b.w. of $Ni(NO_3)_2.6H_2O$ in 14 parts b.w. of $H_2O$; the whole was then extruded, dried and activated as in example 8 and 30 cm³ of the catalyst were tested as in example 7. Data and results (after 6, 24, 120 and 240 hours) are reported in Table 11.

| d (Å) | I/I₀ | d (Å) | I/I₀ | d (Å) | I/I₀ | d (Å) | I/I₀ | d (Å) | I/I₀ |
| --- | --- | --- | --- | --- | --- | --- | --- | --- | --- |
| 13.51 | 13 | 4.26 | 18 | 2.788 | 1 | 2.007 | 11 | 1.491 | 1 |
| 11.16 | 56 | 4.13 | 4 | 2.733 | 3 | 1.999 | 3 | 1.454 | 2 |
| 10.02 | 29 | 4.08 | 1 | 2.703 | 2 | 1.982 | 1 | 1.436 | 3 |
| 9.79 | 3 | 3.97 | 52 | 2.683 | 1 | 1.962 | 1 | 1.420 | 2 |
| 9.06 | 46 | 3.84 | 98 | 2.659 | 2 | 1.945 | 3 | 1.407 | 2 |
| 7.45 | 16 | 3.83 | 24 | 2.607 | 5 | 1.916 | 2 | 1.396 | 2 |
| 7.08 | 8 | 3.76 | 11 | 2.577 | 2 | 1.906 | 3 | 1.383 | 4 |
| 6.71 | 5 | 3.72 | 39 | 2.545 | 3 | 1.874 | 7 | 1.376 | 7 |
| 6.55 | 42 | 3.65 | 18 | 2.508 | 6 | 1.820 | 10 | 1.374 | 2 |
| 6.37 | 9 | 3.50 | 1 | 2.495 | 3 | 1.806 | 2 | 1.336 | <1 |
| 6.06 | 6 | 3.46 | 53 | 2.458 | 6 | 1.787 | 3 | 1.288 | 1 |
| 6.00 | 13 | 3.37 | 8 | 2.416 | 4 | 1.767 | 1 | 1.258 | 3 |
| 5.78 | 16 | 3.35 | 100 | 2.401 | 2 | 1.757 | 2 | 1.241 | 1 |
| 5.73 | 1 | 3.24 | 1 | 2.283 | 6 | 1.720 | 1 | 1.230 | 1 |
| 5.57 | 14 | 3.216 | 30 | 2.238 | 3 | 1.713 | 2 | 1.220 | <1 |
| 5.42 | 1 | 3.195 | 8 | 2.216 | 1 | 1.690 | 2 | 1.212 | 2 |
| 5.14 | 6 | 3.140 | 3 | 2.200 | 1 | 1.673 | 5 | 1.200 | 3 |
| 5.00 | 8 | 3.089 | 3 | 2.173 | 1 | 1.662 | 2 | | |

-continued

| d (Å) | I/I₀ | d (Å) | I/I₀ | d (Å) | I/I₀ | d (Å) | I/I₀ | d (Å) | I/I₀ |
|---|---|---|---|---|---|---|---|---|---|
| 4.85 | 2 | 3.053 | 11 | 2.131 | 4 | 1.641 | 1 | | |
| 4.69 | 2 | 2.984 | 12 | 2.114 | 1 | 1.624 | 1 | | |
| 4.60 | 9 | 2.945 | 6 | 2.108 | 1 | 1.614 | 2 | | |
| 4.51 | 38 | 2.924 | 1 | 2.080 | 2 | 1.591 | 2 | | |
| 4.45 | 1 | 2.880 | 13 | 2.065 | 1 | 1.564 | 2 | | |
| 4.37 | 7 | 2.856 | 2 | 2.036 | 1 | 1.542 | 8 | | |
| — | — | — | — | 2.028 | 5 | 1.519 | 3 | | |

TABLE 2

| d (Å) | I/I₀ | d (Å) | I/I₀ | d (Å) | I/I₀ | d (Å) | I/I₀ | d (Å) | I/I₀ |
|---|---|---|---|---|---|---|---|---|---|
| 13.51 | 13 | 4.13 | 1 | 2.726 | 1 | 1.942 | 2 | 1.383 | 3 |
| 11.16 | 68 | 4.08 | 1 | 2.703 | 1 | 1.917 | 1 | 1.376 | 5 |
| 10.02 | 35 | 3.96 | 20 | 2.683 | 1 | 1.904 | 1 | 1.374 | 1 |
| 9.76 | 3 | 3.84 | 48 | 2.659 | 1 | 1.869 | 3 | 1.344 | 1 |
| 9.06 | 30 | 3.83 | 28 | 2.607 | 3 | 1.820 | 10 | 1.289 | 1 |
| 8.14 | 1 | 3.75 | 4 | 2.545 | 1 | 1.784 | 1 | 1.254 | 2 |
| 7.45 | 1 | 3.72 | 23 | 2.504 | 4 | 1.767 | 1 | 1.242 | 1 |
| 7.11 | 1 | 3.65 | 7 | 2.491 | 2 | 1.754 | 1 | 1.229 | 1 |
| 6.69 | 5 | 3.51 | 1 | 2.458 | 6 | 1.714 | 1 | 1.226 | 1 |
| 6.55 | 19 | 3.46 | 22 | 2.416 | 2 | 1.687 | 1 | 1.210 | 2 |
| 6.35 | 7 | 3.35 | 100 | 2.392 | 2 | 1.673 | 4 | 1.200 | 3 |
| 6.00 | 14 | 3.27 | 1 | 2.279 | 6 | 1.658 | 3 | | |
| 5.78 | 6 | 3.25 | 1 | 2.238 | 2 | 1.610 | 1 | | |
| 5.71 | 2 | 3.215 | 12 | 2.211 | 1 | 1.588 | 1 | | |
| 5.57 | 8 | 3.195 | 4 | 2.200 | 1 | 1.562 | 1 | | |
| 5.42 | 1 | 3.137 | 1 | 2.159 | 1 | 1.542 | 7 | | |
| 5.36 | 1 | 3.085 | 1 | 2.131 | 5 | 1.515 | 1 | | |
| 5.14 | 2 | 3.048 | 5 | 2.108 | 1 | 1.487 | 1 | | |
| 5.00 | 7 | 2.978 | 8 | 2.078 | <1 | 1.471 | 1 | | |
| 4.84 | 1 | 2.945 | 3 | 2.067 | <1 | 1.450 | 2 | | |
| 4.69 | 1 | 2.920 | 2 | 2.028 | 2 | 1.447 | 2 | | |
| 4.60 | 5 | 2.880 | 4 | 2.007 | 5 | 1.433 | 1 | | |
| 4.51 | 13 | 2.867 | 1 | 1.993 | 5 | 1.420 | 2 | | |
| 4.36 | 5 | 2.784 | 1 | 1.981 | <1 | 1.396 | 1 | | |
| 4.26 | 22 | 2.776 | 1 | — | — | — | — | | |

TABLE 3

| d (Å) | I/I₀ | d (Å) | I/I₀ | d (Å) | I/I₀ | d (Å) | I/I₀ | d (Å) | I/I₀ |
|---|---|---|---|---|---|---|---|---|---|
| 13.51 | 4 | 4.13 | 2 | 2.703 | 1 | 1.962 | 1 | 1.420 | 1 |
| 11.16 | 38 | 4.08 | 1 | 2.683 | 1 | 1.945 | 2 | 1.407 | 1 |
| 10.02 | 18 | 3.97 | 17 | 2.659 | 1 | 1.916 | 2 | 1.396 | 1 |
| 9.79 | 5 | 3.83 | 72 | 2.607 | 4 | 1.910 | 1 | 1.383 | 2 |
| 9.06 | 18 | 3.82 | 24 | 2.574 | 1 | 1.874 | 4 | 1.376 | 2 |
| 7.45 | 11 | 3.75 | 7 | 2.545 | 2 | 1.820 | 10 | 1.374 | 5 |
| 7.08 | 6 | 3.72 | 26 | 2.508 | 4 | 1.806 | 1 | 1.336 | <1 |
| 6.71 | 3 | 3.65 | 11 | 2.495 | 3 | 1.787 | 1 | 1.288 | 1 |
| 6.55 | 16 | 3.50 | 1 | 2.458 | 6 | 1.767 | 1 | 1.257 | 2 |
| 6.38 | 6 | 3.46 | 20 | 2.416 | 2 | 1.757 | 1 | 1.241 | <1 |
| 6.06 | 3 | 3.37 | 9 | 2.401 | 1 | 1.720 | 1 | 1.232 | 1 |
| 6.00 | 10 | 3.35 | 100 | 2.283 | 6 | 1.713 | 1 | 1.220 | <1 |
| 5.78 | 7 | 3.24 | 1 | 2.238 | 3 | 1.690 | 1 | 1.212 | 1 |
| 5.73 | 1 | 3.216 | 8 | 2.216 | 1 | 1.673 | 4 | 1.200 | 2 |
| 5.57 | 10 | 3.195 | 5 | 2.200 | 1 | 1.662 | 3 | | |
| 5.42 | 1 | 3.142 | 1 | 2.173 | 1 | 1.641 | <1 | | |
| 5.37 | 1 | 3.089 | 1 | 2.131 | 5 | 1.624 | <1 | | |
| 5.14 | 4 | 3.053 | 6 | 2.108 | 1 | 1.614 | 1 | | |
| 5.01 | 5 | 2.984 | 9 | 2.080 | 1 | 1.591 | 1 | | |
| 4.85 | 1 | 2.945 | 3 | 2.070 | 1 | 1.564 | 1 | | |
| 4.61 | 6 | 2.924 | 1 | 2.036 | 1 | 1.542 | 7 | | |
| 4.51 | 14 | 2.880 | 5 | 2.028 | 1 | 1.520 | 1 | | |
| 4.45 | 1 | 2.856 | 2 | 2.007 | 2 | 1.489 | 1 | | |
| 4.37 | 5 | 2.788 | 1 | 1.999 | 7 | 1.454 | 3 | | |
| 4.26 | 24 | 2.733 | 1 | 1.982 | 1 | 1.436 | 1 | | |

TABLE 4

| d (Å) | I/I₀ | d (Å) | I/I₀ | d (Å) | I/I₀ | d (Å) | I/I₀ | d (Å) | I/I₀ |
|---|---|---|---|---|---|---|---|---|---|
| 13.51 | 7 | 3.96 | 15 | 2.455 | 7 | 1.714 | 1 | 1.228 | 1 |
| 11.16 | 50 | 3.84 | 48 | 2.416 | 2 | 1.689 | 1 | 1.225 | 1 |
| 10.02 | 29 | 3.83 | 21 | 2.392 | 2 | 1.672 | 5 | 1.210 | 1 |
| 9.79 | 3 | 3.75 | 5 | 2.281 | 6 | 1.659 | 3 | 1.200 | 2 |
| 9.06 | 19 | 3.71 | 24 | 2.259 | 1 | 1.625 | 1 | | |
| 7.40 | 1 | 3.64 | 8 | 2.238 | 2 | 1.610 | 1 | | |
| 7.05 | 1 | 3.46 | 19 | 2.211 | 1 | 1.588 | 1 | | |

TABLE 4-continued

| d (Å) | I/I$_o$ | d (Å) | I/I$_o$ | d (Å) | I/I$_o$ | d (Å) | I/I$_o$ | d (Å) | I/I$_o$ |
|---|---|---|---|---|---|---|---|---|---|
| 6.69 | 4 | 3.35 | 100 | 2.200 | <1 | 1.583 | 1 | | |
| 6.55 | 14 | 3.26 | 1 | 2.170 | 1 | 1.564 | 1 | | |
| 6.35 | 7 | 3.215 | 8 | 2.126 | 5 | 1.541 | 7 | | |
| 6.00 | 12 | 3.195 | 4 | 2.099 | 1 | 1.519 | 1 | | |
| 5.78 | 4 | 3.131 | 2 | 2.075 | 1 | 1.514 | 1 | | |
| 5.72 | 2 | 3.085 | 1 | 2.067 | 1 | 1.488 | 1 | | |
| 5.56 | 8 | 3.048 | 6 | 2.028 | 2 | 1.458 | 1 | | |
| 5.36 | 1 | 2.975 | 7 | 2.007 | 3 | 1.451 | 1 | | |
| 5.14 | 2 | 2.936 | 3 | 1.992 | 5 | 1.445 | 1 | | |
| 5.00 | 5 | 2.880 | 4 | 1.981 | 1 | 1.435 | 1 | | |
| 4.84 | 1 | 2.784 | 1 | 1.942 | 2 | 1.420 | 1 | | |
| 4.72 | <1 | 2.726 | 1 | 1.917 | 1 | 1.396 | 1 | | |
| 4.60 | 4 | 2.679 | 1 | 1.904 | 1 | 1.383 | 4 | | |
| 4.51 | 10 | 2.655 | 1 | 1.869 | 3 | 1.372 | 6 | | |
| 4.35 | 5 | 2.607 | 3 | 1.820 | 10 | 1.288 | 1 | | |
| 4.26 | 24 | 2.545 | 1 | 1.784 | 1 | 1.286 | 1 | | |
| 4.12 | 1 | 2.504 | 1 | 1.768 | 1 | 1.256 | 2 | | |
| 4.08 | 1 | 2.488 | 3 | 1.755 | 1 | 1.240 | 1 | | |

TABLE 5

| d (Å) | I/I$_o$ | d (Å) | I/I$_o$ | d (Å) | I/I$_o$ | d (Å) | I/I$_o$ | d (Å) | I/I$_o$ |
|---|---|---|---|---|---|---|---|---|---|
| 13.51 | 4 | 4.37 | 2 | 2.880 | 4 | 2.028 | 1 | 1.521 | 1 |
| 11.16 | 11 | 4.26 | 20 | 2.856 | 1 | 2.007 | 3 | 1.492 | 1 |
| 10.02 | 6 | 4.13 | 1 | 2.788 | <1 | 1.999 | 2 | 1.454 | 2 |
| 9.79 | 1 | 4.08 | <1 | 2.733 | <1 | 1.982 | 3 | 1.437 | <1 |
| 9.06 | 10 | 3.97 | 10 | 2.703 | <1 | 1.962 | <1 | 1.420 | 1 |
| 7.45 | 3 | 3.84 | 29 | 2.687 | 1 | 1.945 | 1 | 1.407 | 1 |
| 7.28 | 1 | 3.83 | 6 | 2.659 | <1 | 1.916 | 1 | 1.395 | 1 |
| 7.08 | 2 | 3.75 | 1 | 2.607 | 1 | 1.910 | 1 | 1.383 | 4 |
| 6.71 | 1 | 3.72 | 9 | 2.577 | <1 | 1.874 | 1 | 1.376 | 2 |
| 6.55 | 8 | 3.65 | 3 | 2.545 | 1 | 1.820 | 10 | 1.375 | 6 |
| 6.38 | 2 | 3.56 | <1 | 2.508 | 2 | 1.802 | 3 | 1.336 | 2 |
| 6.06 | 1 | 3.50 | <1 | 2.495 | 1 | 1.787 | 1 | 1.290 | 2 |
| 6.00 | 3 | 3.46 | 18 | 2.458 | 7 | 1.767 | 1 | 1.258 | 2 |
| 5.78 | 4 | 3.37 | 4 | 2.416 | 1 | 1.757 | 1 | 1.241 | <1 |
| 5.73 | 1 | 3.35 | 100 | 2.401 | <1 | 1.726 | 2 | 1.230 | 1 |
| 5.57 | 4 | 3.27 | <1 | 2.283 | 7 | 1.713 | <1 | 1.220 | 1 |
| 5.42 | <1 | 3.24 | <1 | 2.238 | 3 | 1.690 | <1 | 1.212 | <1 |
| 5.37 | 1 | 3.216 | 6 | 2.216 | 1 | 1.673 | 4 | 1.201 | 2 |
| 5.14 | 2 | 3.195 | 2 | 2.173 | <1 | 1.662 | 2 | | |
| 5.00 | 2 | 3.140 | 1 | 2.131 | 4 | 1.641 | <1 | | |
| 4.85 | 1 | 3.089 | <1 | 2.114 | 8 | 1.624 | <1 | | |
| 4.69 | 1 | 3.053 | 2 | 2.108 | <1 | 1.614 | 1 | | |
| 4.60 | 2 | 2.984 | 14 | 2.080 | <1 | 1.591 | 1 | | |
| 4.51 | 8 | 2.945 | 1 | 2.070 | <1 | 1.563 | 1 | | |
| 4.45 | <1 | 2.921 | <1 | 2.036 | 1 | 1.543 | 7 | | |

TABLE 6

| d (Å) | I/I$_o$ | d (Å) | I/I$_o$ | d (Å) | I/I$_o$ | d (Å) | I/I$_o$ | d (Å) | I/I$_o$ |
|---|---|---|---|---|---|---|---|---|---|
| 13.51 | 3 | 4.10 | <1 | 2.729 | 1 | 1.994 | 2 | 1.462 | 1 |
| 11.16 | 19 | 4.06 | <1 | 2.700 | 1 | 1.982 | 3 | 1.454 | 2 |
| 10.02 | 11 | 3.97 | 8 | 2.659 | <1 | 1.963 | <1 | 1.436 | <1 |
| 9.77 | 2 | 3.85 | 18 | 2.607 | 1 | 1.945 | 1 | 1.420 | 1 |
| 9.05 | 9 | 3.83 | 9 | 2.577 | <1 | 1.922 | <1 | 1.406 | <1 |
| 7.45 | 1 | 3.75 | 1 | 2.545 | 1 | 1.910 | 1 | 1.396 | 1 |
| 7.32 | <1 | 3.72 | 9 | 2.503 | 2 | 1.871 | 2 | 1.383 | 3 |
| 7.08 | <1 | 3.65 | 3 | 2.491 | 1 | 1.840 | <1 | 1.376 | 2 |
| 6.70 | 1 | 3.56 | <1 | 2.458 | 6 | 1.820 | 11 | 1.375 | 6 |
| 6.55 | 7 | 3.50 | <1 | 2.416 | 1 | 1.787 | 1 | 1.290 | 1 |
| 6.35 | 2 | 3.46 | 11 | 2.401 | 1 | 1.767 | <1 | 1.257 | 2 |
| 5.99 | 5 | 3.39 | 2 | 2.342 | <1 | 1.758 | <1 | 1.243 | <1 |
| 5.78 | 3 | 3.35 | 100 | 2.327 | <1 | 1.748 | <1 | 1.229 | 1 |
| 5.73 | 1 | 3.27 | <1 | 2.283 | 6 | 1.727 | <1 | 1.211 | 1 |
| 5.57 | 3 | 3.24 | 1 | 2.238 | 3 | 1.714 | <1 | 1.201 | 2 |
| 5.37 | <1 | 3.216 | 6 | 2.216 | <1 | 1.690 | <1 | | |
| 5.14 | 1 | 3.198 | 1 | 2.173 | <1 | 1.673 | 3 | | |
| 5.00 | 2 | 3.141 | 1 | 2.131 | 5 | 1.662 | 2 | | |
| 4.84 | <1 | 3.089 | 1 | 2.106 | <1 | 1.641 | <1 | | |
| 4.69 | <1 | 3.051 | 2 | 2.080 | <1 | 1.623 | <1 | | |
| 4.59 | 1 | 2.981 | 3 | 2.065 | <1 | 1.613 | 1 | | |
| 4.51 | 6 | 2.945 | 1 | 2.036 | <1 | 1.591 | <1 | | |
| 4.36 | 2 | 2.917 | <1 | 2.028 | 1 | 1.543 | 7 | | |
| 4.26 | 20 | 2.880 | 3 | 2.007 | 2 | 1.519 | 1 | | |
| 4.13 | <1 | 2.788 | <1 | — | — | — | — | — | — |

TABLE 7 (*)

| Catalyst | Feeding % by weight melaxi-lene | Feeding % by weight ethyl-ben-zene | Operative conditions LHSV (h⁻¹) | Operative conditions Temp. °C. | Ap-proach equilib. | Loss C₈ arom. % b.w. | Conversion ethyl-benzene % b.w. | % by weight of products (**) meta-xylene | para-xy-lene | or-tho-xy-lene | ethyl-ben-zene | ben-zene | tolu-ene | higher aro-matics |
|---|---|---|---|---|---|---|---|---|---|---|---|---|---|---|
| Ex. 2 | 89.1 | 10.9 | 2.0 | 300 | 89.0 | 2.7 | 15.2 | 57.0 | 18.7 | 12.2 | 9.4 | 0.8 | 1.1 | 0.8 |
| Ex. 2 | 89.1 | 10.9 | 2.0 | 325 | 89.8 | 4.0 | 20.4 | 56.6 | 19.0 | 13.1 | 8.3 | 1.4 | 1.2 | 0.4 |
| Ex. 2 | 89.1 | 10.9 | 4.2 | 350 | 90.9 | 5.4 | 39.9 | 54.4 | 18.9 | 14.4 | 7.0 | 2.1 | 1.5 | 1.7 |
| Ex. 2 | 89.1 | 10.9 | 4.1 | 375 | 91.8 | 7.6 | 49.7 | 52.6 | 18.8 | 15.5 | 5.6 | 3.0 | 2.2 | 2.3 |
| Ex. 2 | 89.1 | 10.9 | 2.1 | 375 | 92.8 | 12.1 | 68.6 | 48.8 | 18.4 | 16.9 | 3.8 | 4.1 | 3.9 | 4.1 |
| Ex. 4 | 90.6 | 9.4 | 2.1 | 300 | 83.9 | 1.5 | 17.8 | 62.3 | 18.1 | 9.8 | 8.3 | 0.7 | 0.6 | 0.2 |
| Ex. 4 | 90.6 | 9.4 | 2.0 | 325 | 88.2 | 2.3 | 25.6 | 59.1 | 19.0 | 12.6 | 7.0 | 1.3 | 0.7 | 0.3 |
| Ex. 4 | 90.6 | 9.4 | 3.8 | 350 | 91.1 | 3.5 | 34.3 | 56.9 | 19.5 | 14.0 | 6.2 | 1.7 | 0.9 | 0.8 |
| Ex. 4 | 90.6 | 9.4 | 2.0 | 350 | 92.9 | 5.8 | 51.6 | 52.8 | 19.7 | 16.9 | 4.9 | 2.6 | 1.8 | 1.3 |
| Ex. 4 | 90.6 | 9.4 | 6.0 | 375 | 92.3 | 5.1 | 44.6 | 54.8 | 19.5 | 15.2 | 5.0 | 2.6 | 1.7 | 1.2 |
| Ex. 6 | 100 | — | 2.0 | 300 | 91.7 | 1.1 | / | 64.6 | 21.7 | 12.6 | 0 | 0 | 0.6 | 0.5 |
| Ex. 6 | 100 | — | 2.0 | 325 | 96.5 | 2.7 | / | 57.9 | 22.4 | 17.1 | 0 | <0.1 | 1.3 | 1.3 |
| Ex. 6 | 100 | — | 4.0 | 350 | 96.6 | 3.8 | / | 56.2 | 22.2 | 17.9 | 0 | <0.1 | 1.9 | 1.8 |
| Ex. 6 | 100 | — | 6.0 | 375 | 95.8 | 5.4 | / | 54.8 | 21.6 | 18.2 | 0 | 0.1 | 2.6 | 2.7 |
| Ex. 6 (***) | 100 | — | 4.0 | 375 | 97.0 | 6.2 | / | 52.7 | 21.6 | 19.4 | 0 | 0.1 | 3.1 | 3.1 |
| Ex. 8 | 100 | — | 6.0 | 350 | 100.0 | 2.2 | / | 55.6 | 23.2 | 19.1 | 0 | <0.1 | 1.3 | 0.8 |
| Ex. 10 (****) | 100 | — | 6.0 | 325 | 97.5 | 0.6 | / | 53.7 | 23.1 | 22.6 | 0 | 0 | 0.4 | 0.2 |
| Ex. 11 after 24 hrs | 100 | — | 5.0 | 325 | 99.3 | 2.9 | / | 52.7 | 23.0 | 21.5 | 0 | <0.1 | 1.5 | 1.3 |
| after 360 hrs | 100 | — | 5.0 | 325 | 99.5 | 1.1 | / | 53.9 | 23.4 | 21.5 | 0 | 0 | 0.7 | 0.5 |

(*) All the tests were carried out at 15 atm. and with H₂O/hydrocarbon molar ratios = 5; data were determined after 2 hours run
(**) Non-aromatic liquid products: 0.1%; gaseous products absent
(***) H-zeolite extruded with 10% bentonite and then impregnated with 1.1% Nickel before use, in order to reach a longer life
(****) H-zeolite mixed with 10% b.w. of bentonite and 1.1% Nickel and then extruded

TABLE 8

| d (Å) | I/I₀ | d (Å) | I/I₀ | d (Å) | I/I₀ | d (Å) | I/I₀ | d (Å) | I/I₀ | d (Å) | I/I₀ |
|---|---|---|---|---|---|---|---|---|---|---|---|
| 13.51 | 3 | 3.216 | 3 | 1.874 | 1 | 4.60 | 2 | 2.458 | 7 | 1.395 | 1 |
| 11.16 | 13 | 3.192 | 3 | 1.820 | 11 | 4.51 | 3 | 2.416 | 1 | 1.383 | 5 |
| 10.01 | 7 | 3.140 | 1 | 1.802 | 1 | 4.45 | 1 | 2.397 | 1 | 1.376 | 2 |
| 9.79 | 2 | 3.099 | 1 | 1.787 | 1 | 4.36 | 2 | 2.283 | 7 | 1.375 | 6 |
| 9.05 | 4 | 3.053 | 2 | 1.768 | 1 | 4.26 | 22 | 2.238 | 3 | 1.335 | 1 |
| 7.45 | 3 | 2.980 | 4 | 1.757 | 1 | 4.13 | 1 | 2.202 | 1 | 1.290 | 1 |
| 7.07 | 2 | 2.947 | 1 | 1.713 | 1 | 4.08 | 1 | 2.170 | 1 | 1.258 | 2 |
| 6.71 | 1 | 2.921 | 1 | 1.694 | 1 | 3.97 | 5 | 2.131 | 5 | 1.241 | 1 |
| 6.55 | 3 | 2.880 | 1 | 1.673 | 4 | 3.84 | 30 | 2.114 | 1 | 1.230 | 1 |
| 6.38 | 3 | 2.856 | 1 | 1.662 | 2 | 3.83 | 5 | 2.094 | 1 | 1.217 | 1 |
| 6.05 | 2 | 2.788 | 1 | 1.622 | 1 | 3.75 | 4 | 2.075 | 1 | 1.211 | 1 |
| 5.99 | 3 | 2.729 | 1 | 1.614 | 1 | 3.72 | 8 | 2.070 | 1 | 1.201 | 2 |
| 5.78 | 1 | 2.703 | 1 | 1.591 | 1 | 3.65 | 6 | 2.040 | 1 | | |
| 5.71 | 2 | 2.687 | 1 | 1.565 | 1 | 3.50 | 1 | 2.007 | 2 | | |
| 5.57 | 4 | 2.656 | 1 | 1.543 | 7 | 3.46 | 6 | 1.995 | 3 | | |
| 5.42 | 1 | 2.607 | 1 | 1.521 | 1 | 3.37 | 2 | 1.982 | 4 | | |
| 5.37 | 1 | 2.573 | 1 | 1.491 | 1 | 3.35 | 100 | 1.947 | 1 | | |
| 5.14 | 1 | 2.545 | 1 | 1.454 | 2 | 3.27 | 1 | 1.917 | 1 | | |
| 5.00 | 2 | 2.508 | 1 | 1.420 | 1 | 3.24 | 1 | 1.912 | 1 | | |
| 4.85 | 1 | 2.491 | 1 | 1.408 | 1 | | | | | | |

TABLE 9

| d (Å) | I/I₀ | d (Å) | I/I₀ | d (Å) | I/I₀ | d (Å) | I/I₀ | d (Å) | I/I₀ |
|---|---|---|---|---|---|---|---|---|---|
| 13.51 | 3 | 4.12 | 1 | 2.656 | 1 | 1.912 | 2 | 1.363 | 1 |
| 11.16 | 43 | 4.08 | 1 | 2.607 | 4 | 1.874 | 4 | 1.288 | 2 |
| 10.01 | 25 | 3.97 | 10 | 2.573 | 2 | 1.843 | 1 | 1.258 | 2 |
| 9.79 | 2 | 3.84 | 88 | 2.549 | 2 | 1.820 | 11 | 1.241 | 1 |
| 8.98 | 11 | 3.83 | 22 | 2.508 | 5 | 1.769 | 1 | 1.230 | 1 |
| 7.44 | 13 | 3.75 | 8 | 2.491 | 2 | 1.758 | 1 | 1.211 | 1 |
| 7.07 | 6 | 3.72 | 23 | 2.458 | 6 | 1.713 | 1 | | |
| 6.71 | 3 | 3.65 | 15 | 2.415 | 3 | 1.694 | 1 | | |
| 6.55 | 6 | 3.46 | 15 | 2.397 | 2 | 1.671 | 5 | | |
| 6.38 | 9 | 3.37 | 6 | 2.281 | 6 | 1.661 | 3 | | |
| 6.05 | 2 | 3.34 | 100 | 2.238 | 3 | 1.614 | 1 | | |
| 5.99 | 11 | 3.24 | 1 | 2.202 | <1 | 1.565 | 1 | | |
| 5.76 | 2 | 3.216 | 5 | 2.170 | <1 | 1.543 | 6 | | |
| 5.71 | 6 | 3.192 | 5 | 2.127 | 4 | 1.521 | 1 | | |
| 5.57 | 11 | 3.140 | 2 | 2.114 | 2 | 1.497 | 1 | | |
| 5.37 | 1 | 3.052 | 9 | 2.076 | 2 | 1.489 | 1 | | |
| 5.14 | 5 | 2.980 | 11 | 2.067 | 2 | 1.454 | 3 | | |
| 5.00 | 5 | 2.947 | 4 | 2.032 | 2 | 1.420 | 2 | | |
| 4.60 | 6 | 2.880 | 3 | 2.007 | 3 | 1.411 | 1 | | |
| 4.50 | 9 | 2.856 | 1 | 1.995 | 10 | 1.396 | 1 | | |
| 4.36 | 6 | 2.788 | 1 | 1.982 | 2 | 1.384 | 4 | | |

TABLE 9-continued

| d (Å) | I/Iₒ | d/(Å) | I/Iₒ | d (Å) | I/Iₒ | d (Å) | I/Iₒ | d (Å) | I/Iₒ |
|---|---|---|---|---|---|---|---|---|---|
| 4.26 | 23 | 2.726 | 2 | 1.947 | 2 | 1.377 | 3 | | |
| | | | | 1.917 | 1 | 1.373 | 5 | | |

TABLE 10

| d (Å) | I/Iₒ | d (Å) | I/Iₒ | d (Å) | I/Iₒ | d (Å) | I/Iₒ |
|---|---|---|---|---|---|---|---|
| 13.51 | 3 | 4.08 | 1 | 2.508 | 2 | 1.661 | 2 |
| 11.16 | 20 | 3.97 | 7 | 2.491 | 2 | 1.614 | 1 |
| 10.01 | 10 | 3.84 | 40 | 2.458 | 7 | 1.565 | 1 |
| 9.79 | 2 | 3.82 | 10 | 3.415 | 1 | 1.543 | 8 |
| 8.98 | 6 | 3.75 | 3 | 2.397 | 1 | 1.521 | 1 |
| 7.44 | 5 | 3.72 | 13 | 2.282 | 7 | 1.489 | 1 |
| 7.07 | 3 | 3.65 | 8 | 2.238 | 3 | 1.454 | 2 |
| 6.71 | 2 | 3.46 | 9 | 2.131 | 6 | 1.420 | 1 |
| 6.55 | 5 | 3.34 | 100 | 2.110 | 1 | 1.408 | <1 |
| 6.38 | 5 | 3.24 | 1 | 2.076 | <1 | 1.396 | 1 |
| 6.05 | 2 | 3.216 | 3 | 2.067 | 1 | 1.384 | 4 |
| 5.99 | 4 | 3.192 | 2 | 2.032 | 1 | 1.377 | 7 |
| 5.78 | 1 | 3.140 | 1 | 2.007 | 2 | 1.374 | 2 |
| 5.71 | 3 | 3.053 | 4 | 1.995 | 4 | 1.290 | 2 |
| 5.57 | 5 | 2.980 | 5 | 1.982 | 2 | 1.258 | 2 |
| 5.37 | 1 | 2.947 | 2 | 1.947 | 1 | 1.230 | 1 |
| 5.14 | 2 | 2.880 | 2 | 1.917 | 1 | 1.201 | 2 |
| 5.00 | 2 | 2.856 | <1 | 1.912 | 1 | | |
| 4.85 | 1 | 2.788 | 1 | 1.874 | 2 | | |
| 4.60 | 3 | 2.726 | 1 | 1.843 | 1 | | |
| 4.51 | 5 | 2.656 | 1 | 1.820 | 13 | | |
| 4.36 | 3 | 2.607 | 2 | 1.805 | <1 | | |
| 4.26 | 26 | 2.573 | 1 | 1.787 | 1 | | |
| 4.13 | 1 | 2.549 | 1 | 1.758 | 1 | | |
| | | | | 1.713 | 1 | | |
| | | | | 1.673 | 4 | | |

TABLE 11(*)

| CATALYST | OPERATIVE CONDITIONS() | | AEQT | | | Loss C₈ arom. % b.w. | % BY WEIGHT OF PRODUCTS(*) | | | | | | |
|---|---|---|---|---|---|---|---|---|---|---|---|---|---|
| | LHSV (h⁻¹) | T (°C.) | meta % b.w. | para % b.w. | ortho % b.w. | | metha-xylene | para-xylene | ortho-xylene | ethyl-benzene | benzene | toluene | higher aromatics |
| Ex. 12 | 6 | 300 | 96.5 | 99.4 | 93.5 | 0.6 | 54.9 | 23.6 | 20.9 | 0.0 | 0.0 | 0.1 | 0.5 |
| Ex. 12 | 6 | 325 | 97.9 | 99.4 | 96.1 | 3.2 | 52.5 | 22.9 | 21.4 | 0.0 | <0.1 | 1.8 | 1.4 |
| Ex. 12 | 6 | 350 | 98.1 | 99.4 | 96.7 | 7.7 | 49.8 | 21.7 | 20.8 | 0.0 | 0.1 | 4.4 | 3.2 |
| Ex. 12 | 6 | 375 | 98.0 | 99.6 | 96.3 | 14.1 | 46.1 | 20.2 | 19.6 | 0.0 | 0.4 | 8.0 | 5.7 |
| Ex. 13 | 6 | 300 | 88.3 | 98.8 | 77.1 | 0.6 | 58.6 | 23.5 | 17.3 | 0.0 | 0.0 | 0.3 | 0.3 |
| Ex. 13 | 6 | 325 | 95.1 | 99.6 | 90.3 | 1.5 | 54.8 | 23.4 | 20.4 | 0.0 | <0.1 | 0.8 | 0.6 |
| Ex. 13 | 6 | 350 | 96.9 | 99.6 | 94.2 | 3.2 | 52.7 | 22.8 | 21.3 | 0.0 | <0.1 | 1.9 | 1.3 |
| Ex. 13 | 6 | 375 | 97.6 | 99.7 | 95.4 | 6.5 | 50.3 | 22.0 | 21.2 | 0.0 | 0.1 | 3.7 | 2.7 |
| Ex. 12(****) | | | | | | | | | | | | | |
| after 6 hrs | 6 | 300 | 94.9 | 99.3 | 90.2 | 2.6 | 54.5 | 23.1 | 19.8 | — | — | 1.4 | 1.1 |
| after 24 hrs | 6 | 300 | 95.1 | 99.1 | 90.7 | 3.0 | 54.2 | 23.0 | 19.8 | — | — | 2.1 | 0.9 |
| after 120 hrs | 6 | 300 | 95.6 | 99.3 | 91.7 | 1.5 | 54.8 | 23.4 | 20.3 | — | — | 0.9 | 0.6 |
| after 240 hrs | 6 | 300 | 95.7 | 100.0 | 90.8 | 1.2 | 54.9 | 23.7 | 20.2 | — | — | 0.7 | 0.5 |

(*)The feed contained 99.80% metaxylene, 0.16% orthoxylene and 0.04 paraxylene
(**)All the tests were carried out at 15 atm. with H₂ : hydrocarbon molar ratios = 5; the data were determined after a 2 hours run
(***)Non-aromatic liquid product: 0.1; gaseous products: absent
(****)H—zeolite mixed with 10% b.w. of bentonite and 1.1% Ni and then extruded

What we claim is:

1. A method for preparing zeolites having the formula:

$(1.5 \pm 0.6)M_{2/n}O.Al_2O_3.ySiO_2.zH_2O$ wherein y ranges from 20 to 90, z ranges from 2 to 12, M is at least one cation and n is the valence of M, and wherein Al and Si can be optionally replaced, at least partially, by Ga and Ge respectively, said method comprising the admixing of diethylpiperidinium hydroxide or of a salt thereof with H₂O and with at least:
  (a) one sodium compound;
  (b) one compound of a metal selected from the group comprising Al, Ga and mixtures thereof;
  (c) one compound of an element selected from the group comprising Si, Ge and mixtures thereof, the molar ratios, expressed as ratios of oxides, being comprised within the following ranges:
  $SiO_2:Al_2O_3$ = from 20 to 120
  $Na_2O:SiO_2$ = from 0.07 to 0.50
  $(DEPP)_2O:SiO_2$ = from 0.05 to 0.50
  $H_2O:Na_2O$ = from 50 to 600, and wherein the resulting start mixture is heated, for crystallization purposes, at from 160° C. to 200° C. for at least 24 hours.

2. A method according to claim 1, characterized by the following ranges of molar ratios:
  $SiO_2:Al_2O_3$ = from 40 to 85
  $Na_2O:SiO_2$ = from 0.07 to 0.25
  $(DEPP)_2O:SiO_2$ = from 0.10 to 0.20
  $H_2O:Na_2O$ = from 150 to 400.

3. A method according to claim 2, wherein the cation dilution ratios are as follows:
  r1 = equal to or higher than 190.
  r2 = equal to or higher than 90.

4. A method according to claim 2, wherein the sodium factor r2:r1 (SF) is from 0.20 to 0.60, and wherein the cation mineralization factor (CMF) is from 0.22 to 0.38.

5. A method according to claim 4, wherein SF is from 0.30 to 0.50 and wherein CMF is from 0.22 to 0.30.

6. A method according to claim 4, wherein SF is from 0.50 to 0.60 and wherein CMF is from 0.22 to 0.30.

7. A method according to claim 4, wherein SF is from 0.30 to 0.50 and wherein CMF is from 0.30 to 0.38.

8. A method according to claim 4, wherein the start mixture is heated, until crystallization, in only one step, at from 180° to 200° C., for at least 24 hours.

9. A method according to claim 4, wherein an aqueous solution is prepared, which contains the DEPP salt, Na aluminate and NaOH, secondly the solution is heated between 60° and 70° C., thirdly a solution containing SiO₂ is added, then the whole is heated for crystallization purposes and finally the crystallized zeolite is washed, dried and activated by means of heating in the air at a temperature from 450° C. to the temperature at which the structural collapse starts.

10. A method according to claim 4, characterized in that the DEPP salt is (DEPP)Br, (a) is NaOH, (b) is Na aluminate and (c) is a silica sol.

* * * * *